United States Patent [19]

Muller et al.

[11] 4,361,026

[45] Nov. 30, 1982

[54] METHOD AND APPARATUS FOR SENSING FLUIDS USING SURFACE ACOUSTIC WAVES

[76] Inventors: Richard S. Muller, 51 Kenyon Ave., Kensington, Calif. 94708; Richard M. White, 350 Panoramic Way, Berkeley, Calif. 94704

[21] Appl. No.: 162,604

[22] Filed: Jun. 24, 1980

[51] Int. Cl.³ .......................................... G01N 31/06
[52] U.S. Cl. ............................................................. 73/23
[58] Field of Search ............. 73/23; 310/313 B, 313 R

[56] References Cited

U.S. PATENT DOCUMENTS

| | | | |
|---|---|---|---|
| 3,266,291 | 8/1966 | King | 73/23 |
| 3,715,911 | 2/1973 | Chuan | 73/23 |
| 3,879,992 | 4/1975 | Bartera | 73/23 |
| 4,055,072 | 10/1977 | Fletcher | 73/23 |
| 4,081,769 | 3/1978 | Shreve | 310/313 B |
| 4,096,740 | 6/1978 | Sallée | 310/313 B |
| 4,100,811 | 7/1978 | Cullen et al. | 73/654 |
| 4,312,228 | 1/1982 | Wohltjen | 73/23 |

OTHER PUBLICATIONS

H. Wohltjen et al., "Surface Acoustic Wave Probes For Chem. Analysis. I. Intro and Instr Description", *Analy. Chem.*, vol. 51, pp. 1458-1464, Aug. 1979.
H. Wohltjen et al., "Surface Acoustic Wave Probes For Chem. Anal. II. Gas Chrom. Detector," *Analy. Chem.*, vol. 51, No. 9, pp. 1465-1470, Aug. 1979.
H. Wohltjen et al., "Surface Acoustic Wave Probes For Chem. Anal. III Thermomech. Polymer Analyzer," *Analy. Chem.* vol. 51, No. 9, pp. 1470-1475, Aug. 1979.
P. K. Ko, *A Capacitive Halothane Detector*, pp. 1-60, May 1978.

*Primary Examiner*—Stephen A. Kreitman
*Attorney, Agent, or Firm*—Phillips, Moore, Lempio & Finley

[57] ABSTRACT

This disclosure relates to a method and apparatus for sensing the presence of gases, vapors, and liquids using surface acoustic waves. At the present time the commercially available devices for measuring the presence of fluids, although fast reacting and generally quite accurate, are very expensive and bulky. Further, these devices do not lend themselves to advanced integrated signal processing and digital techniques. This disclosure describes a precise, fluid sensing unit that is small, easily integrated, and relatively inexpensive to fabricate. The apparatus includes a medium on which surface acoustic waves can be propagated, transmitting and receiving transducers, and a sensing member located across the path of the surface acoustic waves. The sensing member has a physical characteristic that varies the velocity and/or the attenuation of the waves when in the presence of the specific fluid being detected. The presence of the fluid is sensed by the apparatus by measuring the variation in the surface acoustic waves resulting from this interaction.

14 Claims, 11 Drawing Figures

METHOD AND APPARATUS FOR SENSING FLUIDS USING SURFACE ACOUSTIC WAVES

GOVERNMENT CONTRACT

The U.S. Government has rights in this invention pursuant to Grant No. ENG 7822193 awarded by the National Science Foundation.

DESCRIPTION

1. Technical Field

This invention relates generally to fluid sensing systems and more particularly to techniques for sensing the presence of gases, vapors and liquids.

2. Background Art

At the present time the commercially available equipment for measuring the presence of fluids includes spectrometers, gas chromatographs, and resonatrons. The spectrometers operate in the conventional manner and are tuned to detect the atoms of specific gases. The resonatrons measure the resonance of ions in high electric fields and in that way can detect the presence of specific fluids.

In hospital operating rooms the presence of the anesthetic agent halothane is sometimes sensed mechanically. A polymer material is placed in tension and when halothane is present, the plastic properties of the polymer change. These changes are mechanically sensed by lenses and are observable on a mechanical dial. Another fluid sensing concept is the use of mechanical changes in a polymer to vary the capacitance of a parallel plate capacitor. Any change in capacitance generates a measurable electrical parameter.

Although these devices are fast reacting and are generally quite accurate, the individual units are very expensive. Secondly, these systems are usually very bulky and in some applications, like hospital operating rooms, space is a premium. A further problem with prior fluid sensors has been that the sensing element has been designed for operation with analog electrical systems. The output parameters and signals from these sensors do not lend themselves to advanced integrated signal processing and digital techniques.

The present invention is directed to overcoming one or more of the problems as set forth above.

DISCLOSURE OF THE INVENTION

In one aspect of the present invention an apparatus for sensing the presence of a specific fluid is contemplated. The apparatus includes a medium on which surface acoustic waves can be propagated, transmitting and receiving transducers, and a sensing member located across the path of the surface acoustic waves. The sensing member has a physical characteristic that varies the waves when in the presence of the specific fluid being detected and by measuring the variation, the presence of the fluid can be sensed.

In another aspect of the present invention a method for sensing the presence of a specific fluid is contemplated. The method includes propagating surface acoustic waves, interacting these waves with a sensing member, and measuring the change in the waves.

A principal object of the present invention is to provide a precise fluid sensing unit that is small, easily integrated, and relatively inexpensive to fabricate. This object is achieved by using surface acoustic waves that interact with a sensitive member. The member, when in the presence of the fluid being detected, varies the velocity of the waves and/or the attenuation.

A feature of the present invention is that it is easily adaptable to an integrated signal processing system and can generate output signals that are easily recorded and processed.

An additional object of the present invention is to provide a sensor in a completely integrated form. This object is achieved by placing the detector, its amplifying and detecting circuitry, and the transducing elements all on a single semiconductor chip. The chip can be a piezoelectric material such as lithium niobate or quartz (both of which are electrical insulators), or else it can be a nonpiezoelectric semiconductor such as silicon. In this latter case, the piezoelectric property needed to launch and receive surface acoustic waves would be obtained by placing thin films of an active piezoelectric material (such as zinc oxide) under interdigitated transducers.

An additional feature of this invention is that it may be placed in a hostile environment such as in the presence of corrosive vapors or elevated temperatures. This feature is achieved by shielding the sensitive components of the device and remotely locating them from adverse exposure.

Still another feature of the present invention is that the same sensor body can be used with various sensitive members to detect a wide variety of fluids. The same sensor body can be produced in large volume without the sensitive member and stored until needed. Before placing the sensor in service the necessary sensitive material required for the specific application can be applied to the sensor body. This substantially reduces the inventory of parts that a manufacturer need maintain.

BEST MODE FOR CARRYING OUT THE INVENTION

Figure 1:
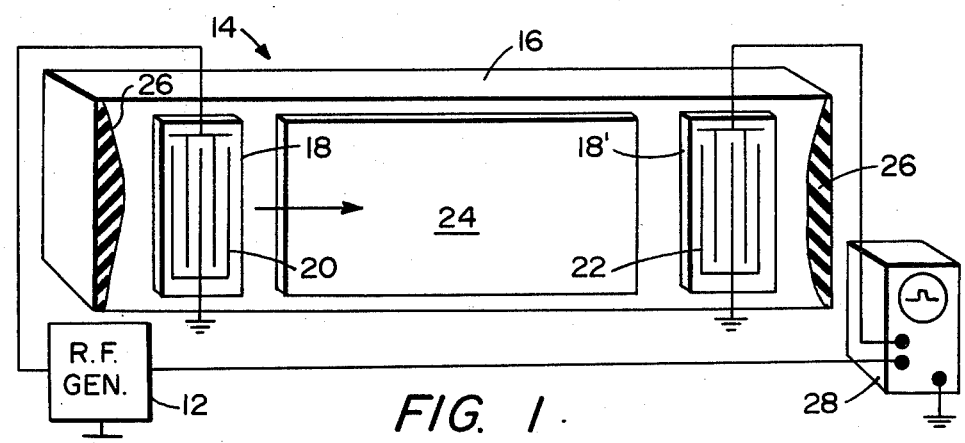
FIG. 1 is a diagrammatic perspective view of one embodiment of the present invention. This embodiment has a single path for surface acoustic waves through a fluid sensitive material.

FIG. 1 illustrates an apparatus for sensing the presence of a specific fluid using surface acoustic waves. The waves are propagated under a sensing member that changes the velocity and/or the attenuation of the waves when in the presence of the fluid. The apparatus includes a conventional RF pulse generator 12. The pulse generator produces an amplitude modulated carrier with a pulse length of approximately one microsecond and a frequency in the megahertz range. In two of the sensors actually constructed the frequencies were 17 and 35 megahertz.

The apparatus further includes a medium 14, FIG. 1 on which surface acoustic waves can be propagated. In FIG. 1 the medium comprises a substrate 16 that is fabricated from a semi-conductor material such as silicon. The use of a semi-conductor material like silicon permits all of the circuits associated with the apparatus to be integrated into the substrate including the RF pulse generator 12 and the oscillator circuits described below. The medium 14 also includes two thin piezoelectric films 18, 18' such as zinc oxide located on the substrate in the regions beneath transducers 20 and 22.

It should also be appreciated that the surface acoustic wave propagating medium 14 can be fabricated entirely from a piezoelectric material such as lithium niobate, quartz or gallium arsenide. In addition, piezoelectric materials fabricated from polymers can be used such as polyvinyl fluoride.

The surface acoustic waves that propagate in the medium 14, FIG. 1 are generated by a transmitting transducer 20 that is driven by the RF generator 12. The transmitting transducer is an interdigitated electrode of conventional construction. The surface acoustic waves propagate on the surface of the medium 14 and travel under and interact with a fluid sensing member 24 described in detail below. The surface acoustic waves are received by a receiving transducer 22 and are converted into electrical signals. The receiving transducer 22 is an interdigitated transducer of known construction. The propagating medium 14 also includes two absorbers 26 located at the ends of the apparatus for absorbing the surface acoustic waves and for preventing reflection.

The sensing member 24, FIG. 1 is a film or layer of material on the propagating medium 14 that is placed in the path of the surface acoustic waves and continuously interacts with them. The sensing member is carefully selected to have a physical characteristic or property that varies a measurable parameter of the waves only when subjected to the specific fluid that the apparatus is designed to detect. The measurable parameters of surface acoustic waves include velocity, phase, transit time, and attenuation. The changes in physical properties which can cause the measurable parameters to change include a change in the elastic constant of the sensing member. For example, some gases chemically react with the member and cause it to harden while other fluids cause the member to become more elastic. A second property that can change is its thickness. For example, in the presence of some fluids the member will swell. It is also possible that the sensing member could partially vaporize by sublimation in some ambients or even react chemically with the gas to be sensed and in this way change its effect on the traveling surface acoustic waves. In addition, a third physical property that can change is density. Changes in density with certain fluids are characteristic of absorbing materials such as those listed below. Further, the fluid to which the member is sensitive may cause a combination of all three effects to occur and hence the parameter being measured can either increase or decrease depending on the composition of the member and the fluid being sensed.

The following is a table of some of some of the materials and fluids which can be used with this apparatus:

| Sensing Materials | Detectable Fluids and Gases |
|---|---|
| RTV silicone rubber | halothane |
| polyvinyl chloride | acetone |
| 30% acrylonitrile (a butadiene acrylonitrile co-polymer) | benzene |
| 15% acrylonitrile (a butadiene acrylonitrile co-polymer) | heptane |
| adiprene C (a polyurethane) | carbon tetrachloride |
| adiprene C (a polyurethane) | ethanol |
| polybutadiene | methyl ethyl ketone |

The sensing member 24 is applied using conventional techniques such as spinning and dipping. Further, roll-on films can also be used. Films may be fastened with adhesives or attached by heating and partial melting of the film. Films may be polymerized in place as by the electron or ion beam bombardment of suitable atoms adsorbed on the surface during the manufacturing process. When in place the member has a thickness that is comparable to or somewhat less than the wave length of the surface acoustic waves that are propagated on the medium 14. It is believed that if the layer 24 is too thick, there will be excessive acoustic energy traveling in the film which may result in unacceptably high attenuation. Further, if the layer 24 is too thick, the minimum time for the fluid to be absorbed in the member will increase and the response of the apparatus will be slowed. It is therefore believed that a thickness of ten microns or less will provide optimum performance. In addition, the thickness of the layer should be constant across the wave front. If uniformity in thickness is not achieved, then distortion will occur and the surface acoustic waves will not interact well with the receiving transducer 22.

Although a substantially uniform planar surface is desirable for the purposes of calibration and uniformity between sensing devices, this is not critical. The interaction between the surface acoustic waves and the sensing member will occur irrespective of any discontinuities in the surface.

In operation, the apparatus illustrated in FIG. 1 is driven by the RF generator 12 which produces an electrical pulse which drives the transmitting transducer 20. The transmitting transducer generates surface acoustic waves so that they propagate along the surface of the medium 14 and are received by the receiving transducer 22. When the surface acoustic waves pass under the sensing member 24, the waves interact with the member and the parameter being measured is varied in accordance with this interaction.

In one embodiment the transit time of the surface acoustic waves between the transmitting and receiving transducers 20, 22 is measured by a timing apparatus 28. In this embodiment the apparatus is an oscilloscope which is triggered by the RF generator 12. The oscilloscope is connected to measure either the transit time of the waves or the phase shift. In an alternative embodiment the attenuation of the surface acoustic waves between the transmitting and receiving transducers is measured using either the oscilloscope 28 or an RF tuned voltmeter. When the controlling physical property of the member is changed by the presence of a fluid being sensed, a measurable variation in the acoustic wave parameter being measured occurs. This variation results in an electrical signal which can be measured and processed digitally.

It is believed that the surface acoustic wave velocity is the measurable parameter that provides the most satisfactory results. Thus, the description of the embodiments that follow only describes measuring velocities. It is to be understood, however, that this is done only for clarity and brevity and is not intended to limit the invention.

Figure 2:
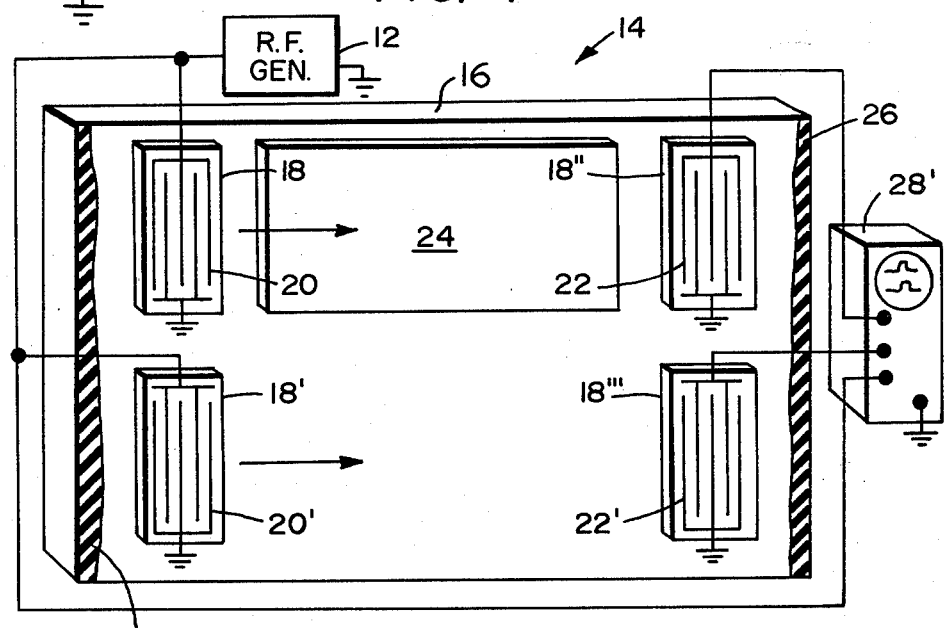
FIG. 2 is a diagrammatic perspective view of a second embodiment of the present invention. This embodiment has two paths for surface acoustic waves, one through a fluid sensitive material and one that is unobstructed.

The embodiment illustrated in FIG. 2 permits any error due to variations in temperature to be eliminated. The apparatus is essentially a duplicate of the apparatus of FIG. 1 except that a second surface acoustic wave path which does not interact with the sensing member 24 is placed on the medium 14. The medium 14 and the transmitting and receiving transducers 20, 20', 22, 22' are identical respectively. Both transmitting transducers 20,20' are driven simultaneously by the RF generator 12 and produce surface acoustic waves that are directed to and are received by the receiving transducers 22, 22'.

In FIG. 2 one surface acoustic wave path runs beneath the sensing member 24 so that the waves interact with the member. The second path does not interact with the member and hence it is not affected by the presence of the fluid that is desired to be detected. Since the velocity of the waves across the medium 14 between the transmitting and receiving transducers is temperature sensitive, the arrival time error can be cancelled out by using two parallel paths of equal length on the same medium. Any difference in arrival time between the waves in the two paths is then due to the presence of the fluid. The receiving transducers 22,22' are connected to a dual trace oscilloscope 28' which measures the changes in velocity and in phase between the two sets of detected waves. In the alternative embodiment the receiving transducers can be connected to a signal subtracting circuit so that no output signal is obtained unless the sensing member 24 is in the presence of the fluid desired to be detected.

Figure 3:
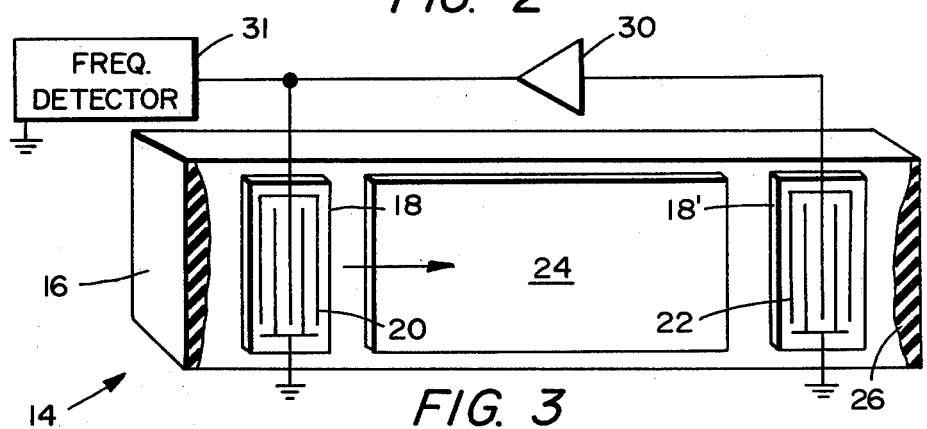
FIG. 3 is a diagrammatic perspective view of a third embodiment of the present invention. This embodiment has a single path for surface acoustic waves through a fluid sensitive material and incorporates an oscillator circuit.

The apparatus in FIG. 3 utilizes a single path for the acoustic waves and forms an oscillator circuit. The apparatus includes an RF generator 12, a medium 14 on which surface acoustic waves are propagated, transmitting and receiving transducers 20,22 and a fluid sensing member 24 which are all constructed and operated in the same manner as described above.

In the embodiment of FIG. 3 the signal detected by the receiving transducer 22 is fed back through an amplifier 30 to the transmitting transducer 20. The amplifier 30 is a conventional amplifier having sufficient gain at the frequency of the surface acoustic waves to make up for the insertion loss between the transmitting and receiving transducers 20,22. The amplifier also has sufficient gain so that the circuit starts from its own noise and an RF generator is not required. The circuit forms a surface acoustic wave oscillator and it is contemplated that the amplifier 30 can be integrated into the silicon substrate 16. The output of the amplifier is connected to a frequency detector or counter 31. In the presence of the fluid to which the member 24 is sensitive, the circuit exhibits a shift in frequency which is detected by the frequency counter.

Figure 4:
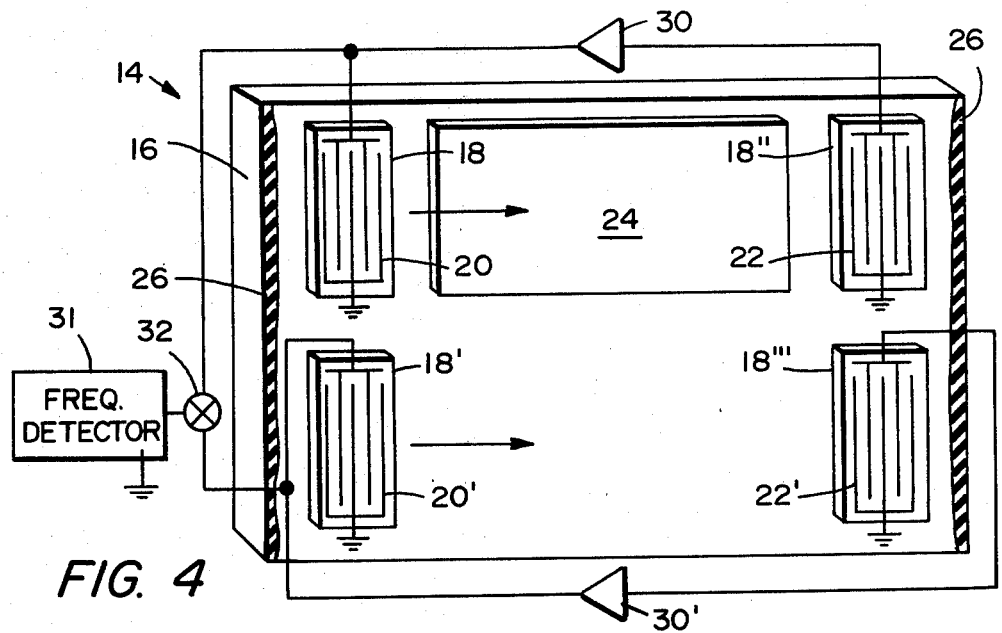
FIG. 4 is a diagrammatic perspective view of a fourth embodiment of the present invention. This embodiment has two paths for surface acoustic waves, one through a fluid sensing material and one that is unobstructed. Each path incorporates an oscillator circuit.

The apparatus illustrated in FIG. 4 provides both temperature compensation and two oscillator circuits for detecting the presence of the fluid. The apparatus is essentially a duplicate of the apparatus of FIG. 2 except for the addition of two oscillator circuits. The surface acoustic waves are propagated along two parallel paths by two interdigitated electrodes 20,20' and are received by interdigitated transducers 22,22'. As in the embodiment of FIG. 2 one path of surface acoustic waves interacts with the sensing member and the other path does not. The outputs from the receiving transducers 22,22' are fed back through two amplifiers 30,30' so that two independent surface acoustic wave oscillator circuits are formed. Compensation for temperature drifts in the material due to temperature sensitivity is achieved by subtracting the two sets of amplifier output signals using a mixer 32. The mixer 32 has an output which is an AC signal having a frequency that is a measure of the change in conditions between the two surface acoustic wave paths in the medium.

Figure 5:
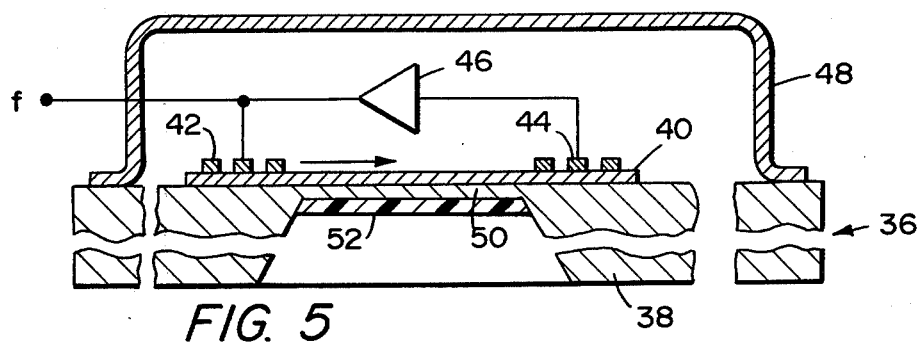
FIG. 5 is a side elevational view, in cross-section and broken away, of a fifth embodiment of the present invention. This embodiment has a single path for surface acoustic waves through a fluid sensitive material. The fluid sensitive material is located on the bottom side of a substrate and the acoustic wave components are located and shielded on the top side of the substrate.
Figure 6:
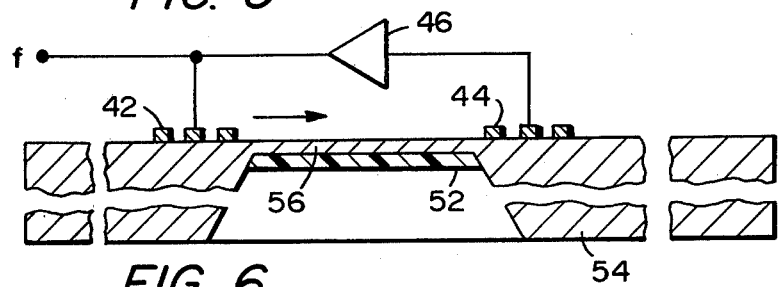
FIG. 6 is a side elevational view, in cross-section and broken away, of a sixth embodiment of the present invention. This embodiment has a single path for surface acoustic waves through a fluid sensitive material and the substrate is a piezoelectric material.
Figure 7:
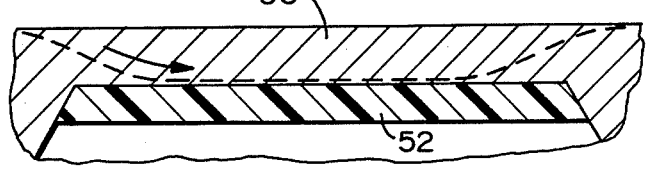
FIG. 7 is an enlarged side elevational view of a portion of FIG. 6.
Figure 8:
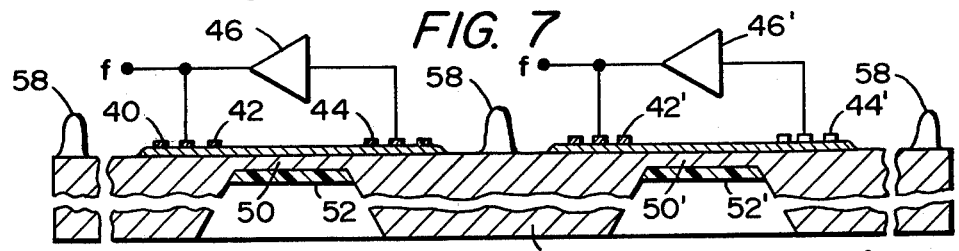
FIG. 8 is a side elevational view in cross-section and broken away of a seventh embodiment of the present invention. This embodiment includes two independent surface acoustic wave paths on a common substrate. Each path incorporates an oscillator circuit.

FIG. 5 illustrates a side elevational view of an alternative apparatus for sensing the presence of a specific fluid in hostile environments. The delicate acoustic wave components are shielded on one side of the propagating medium 36 while the sensitive member 52 is exposed to the environment being sampled. This figure along with FIGS. 6–8 is described as having top and bottom surfaces but this description is merely for the purposes of explanation. The apparatus includes a medium 36 on which surface acoustic waves can be propagated. Typically, the medium comprises a semi-conductor substrate 38 such as silicon and a piezoelectric film 40 such as zinc oxide. Interdigitated transmitting and receiving transducers 42,44 are located on top of piezoelectric layer 40. These transducers are connected to an amplifier 46 to form an acoustic wave oscillator as described above. The delicate surface acoustic wave components are covered by a shield 48 which can be fabricated from metal, ceramic or glass materials. The shield covers the top surface of the substrate 38 and protects all the acoustic wave components from hostile environments such as elevated temperatures, corrosive vapors, and physical contact.

Referring to FIG. 5, the bottom surface of the substrate 38 has been etched away using an orientation dependent etch so that the portion 50 of the substrate under the wave path between the transducers 42,44 has been substantially narrowed. The narrowed portion 50 of the substrate is formed according to conventional semi-conductor processing techniques and is covered by a sensitive member 52 that has a physical characteristic that varies the velocity of the acoustic waves when in the presence of a specific fluid. The surface acoustic waves propagated between the transducers 42,44 interact with the sensitive member if the substrate 38 has been sufficiently thinned so that some acoustic wave energy exists near the bottom surface of the substrate 50. In other words, to the extent that surface acoustic wave energy is present at the bottom surface of the narrowed portion 50 of the semi-conductor substrate, this energy will interact with the sensitive member 52 and its velocity across the narrowed portion 50 will be affected by the properties of the member 52.

Typically, the thickness of the silicon substrate 38 is approximately 250 microns, the thickness of the piezoelectric layer 40 is 5–10 microns, and the narrowed portion 50 of the substrate 1–20 microns. It is believed that the thickness of the narrowed portion 50 of the substrate should be equal to or substantially less than the wavelength of the surface acoustic waves propagated in the apparatus.

FIG. 6 illustrates an alternative embodiment that gives improved surface acoustic wave transmission. In this embodiment the acoustic waves are propagated through a medium 54 which is both a semi-conductor and a piezoelectric material such as galium arsenide. The propagating medium 54 thus does not require a piezoelectric film such as the film 40, FIG. 5. In the embodiment of FIG. 6 the interdigitated electrodes 42,44 are placed directly on the substrate 54 and the acoustic waves propagated between the transducers 42,44 interact with the sensitive member 52 to detect the presence of specific fluids.

The substrate 54, FIG. 6 is etched away in the same manner as described above to form a narrow portion 56. This narrow portion 56 of the substrate is thicker than the dimension of the wavelength of the acoustic waves propagated in the medium 54. It is well-known that if surface acoustic waves are launched on top of such a narrowed portion 56, ultimately the entire energy of the surface waves will reach the bottom of the narrowed portion and will return to the top surface of the substrate after some further distance. This phenomenon shown in FIG. 7 enables the surface wave energy to be more easily propagated through the medium 54 and to interact with the sensitive member 52.

FIG. 8 illustrates an embodiment having a plurality of fluid sensors. Each sensor is constructed and operated in the same manner as the embodiment of FIG. 5. The sensors are separated by absorbers 58 that prevent the acoustic waves in the different paths from interacting. In the embodiment of FIG. 7 each fluid sensor can simultaneously sense a different substance so that a plurality of different substances can be detected. Further, this embodiment is used when it is not possible to find a sensitive member that is uniquely sensitive to a given fluid. By using different members and looking at the relative changes between them, the given fluid can be detected from knowing the relative sensitivities.

The embodiments of FIGS. 5–8 are fabricated by first locating the piezoelectric layer 40 and the interdigitated transducers 42,44 on the substrate 38, 54. Next, if these components operate satisfactorily, then the top surface of the substrate is placed within a cup (not shown) which seals the substrate with an O-ring or other suitable sealing. Then, the entire assembly is dipped into the etchant and etching proceeds in the usual fashion. The use of the cup prevents the etchant from attacking the structure on the top of the substrate. This process is also used because the narrowed portions 50,56 of the substrate have such small thicknesses that the devices become relatively fragile.

Figure 9:
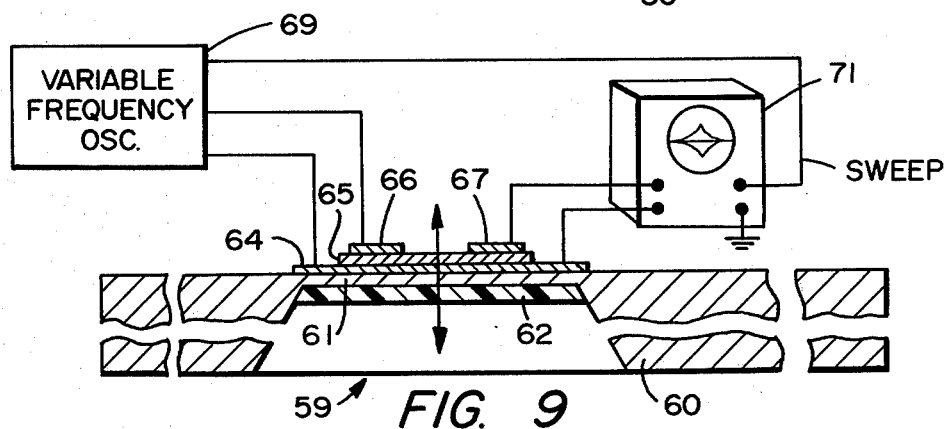
FIG. 9 is a side elevational view, in cross-section and broken away, of an eighth embodiment of the present invention.

FIG. 9 illustrates an alternative embodiment 59 of the present invention wherein a thin membrane is driven at mechanical resonance and the presence of fluid being detected is sensed by changes in the resonance of the apparatus. The apparatus 59 includes a silicon substrate 60 which is etched as described above to form a narrowed portion 61 which acts like a thin membrane. A sensitive member 62 which has a physical characteristic that changes in the presence of the fluid being detected is attached to the bottom surface of the membrane. The top surface of the substrate 60 is covered first by a thin gold electrode 64. This electrode underlies a zinc oxide film 65 which provides the piezoelectric layer. The zinc oxide film is continuous and is surmounted by two electrically independent gold electrodes 66, 67.

One pair of electrodes 64,66, FIG. 9 is connected to a driving circuit which supplies an AC voltage to the zinc oxide film 65 and drives the membrane 61 in a mode of vibration like a drum head. In the preferred embodiment, the driving circuit includes a variable frequency oscillator 69 which can vary the frequency at which the zinc oxide film is driven so that the point of mechanical resonance can be determined.

The other pair of electrodes 64,67, FIG. 9 is connected to a resonance detecting circuit which measures the changes in amplitude of mechanical motion of the thin membrane 61 as detected by the piezoelectric layer 65. In the preferred embodiment the detecting circuit includes an oscilloscope 71 whose horizontal beam deflection is synchronized with changes of the frequency of oscillator 69. As an alternative a network analyzer (not shown) can also be used. The network analyzer measures the phase relationship between the driving voltage and current looking into the piezoelectric layer 65.

The resonance frequency of the membrane 61, FIG. 9 depends, inter alia, upon the elastic properties of the material from which it is made. The resonance frequency also depends on the lateral dimensions of the membrane and upon the elastic properties of the sensitive member 62 which is attached to the bottom wall of the membrane. To the extent that the elastic properties of the sensitive member 62 are important in determining the resonance frequency of the apparatus, any change in these properties due to the presence of a fluid will consequently cause the resonance frequency to change. This leads to a change in the output signal from the oscilloscope 71 which indicates the amount and composition of the fluid present.

An advantage of this embodiment is that the apparatus operates in the high kilohertz frequency range instead of the tens of megahertz range which is common for surface acoustic waves. In this lower frequency range less expensive circuit components and frequency analyzers can be used.

In operation, the variable frequency oscillator 69, FIG. 9 is connected as shown and its output frequency is varied until the resonance frequency of the apparatus is found. The resonance frequency is the frequency at which the maximum amplitude of mechanical motion of the thin membrane 61 occurs. Using the oscilloscope 71 the changes in amplitude are measured as the driving frequency is varied.

Once the frequency of mechanical resonance is determined, the zinc oxide layer 65 is continuously driven at that frequency and the oscilloscope is monitored. If the fluid to which the member 62 is sensitive is brought into the presence of the member, then the mechanical properties of the member 62 change and the resonance frequency of the thin membrane consequently changes. The change in resonance frequency is detected on the oscilloscope 71 as a change in the amplitude of the motion.

Figure 10:
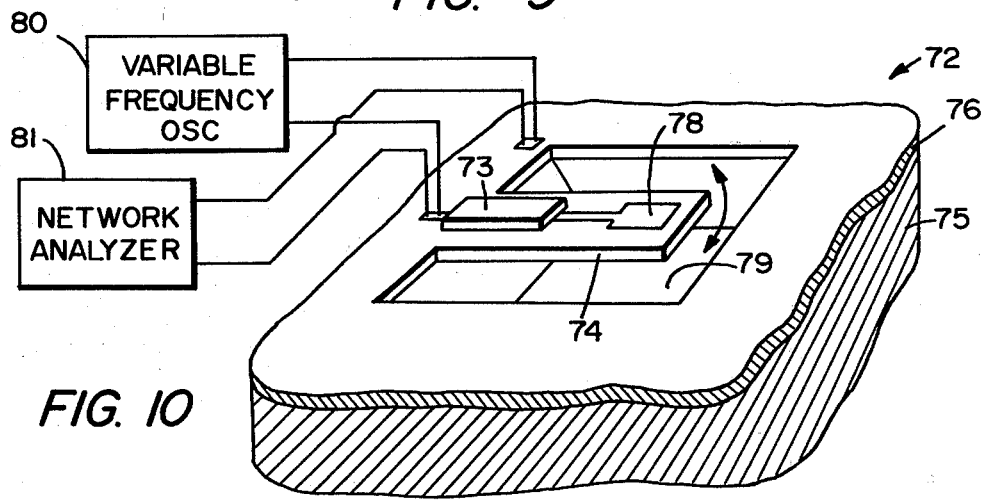
FIG. 10 is a perspective view, in cross-section and broken away, of a ninth embodiment of the present invention.

Referring to FIG. 10, the presence of a specific fluid can also be determined by vibrating a sensitive member 73 using a cantilever 74 and detecting changes in mechanical resonance. The principal advantage of this apparatus 72 is that it is small and can easily be constructed. The cantilever is very thin and is fabricated in place from a silicon wafer 75. The sensitive member 73 is a material specially chosen to have a physical characteristic that when exposed to the fluid to be detected, it will alter the mechanical or acoustical resonance of the cantilever. The sensitive member 73 is positioned on the cantilever 74 at the region of maximum strain. The cantilever is electrostatically driven by placing an AC potential from a variable frequency oscillator 80 between the bottom of the well 79 and the electrode 78 which is positioned at the free end of the cantilever. The substrate 75 is fabricated from conductive silicon and electrode 78 is electrically isloated from it.

It should be noted that the cantilever 74, FIG. 10 can also be driven using a piezoelectric film (not shown). An AC potential is applied to the piezoelectric film and the cantilever is driven at its resonance frequency as described below. It should also be noted that the driving circuit of FIG. 9 which includes the electrodes 64,66 and the piezoelectric layer 65 could also be used to drive the cantilever 74.

The cantilever 74 is formed by first applying a U-shaped mask to the substrate 75. Next the uncovered silicon is oxidized so that a layer 76 of silicon dioxide is formed on the top of the substrate. The U-shaped area covered by the mask remains pure silicon. Thereafter the well 78 is etched in the substrate using a standard silicon etching material. The etchant forms the cantilever 74 by removing the bare silicon and leaving the silicon dioxide layer behind. The cantilever itself is formed from the silicon dioxide layer which is untouched by the etchant. If the top of the substrate 75 is the (100) face of a silicon wafer, then the side walls of the well 78 make an angle of 54° with the bottom of the well. Thereafter the electrode 78 and the sensitive member 73 are applied to the cantilever. In the figure, the sensitive member is positioned at the point of maximum strain on the cantilever so that the change in its elastic properties have a maximum effect on the resonant frequency of the cantilever structure. If the resonant cantilever scheme is used with a sensitive member that undergoes a mass change in the presence of the fluid to be detected, then the most sensitive position would be at the free end of the cantilever.

In operation the apparatus of FIG. 10 is electrostatically driven by the oscillator 80 so that the cantilever 74 vibrates like a reed. The variable frequency oscillator 80 is adjusted so that the resonance frequency of the cantilever is found when the sensitive member 73 is not exposed to the fluid desired to be detected. Mechanical/acoustic resonance of the cantilever is found using either an oscilloscope 71, FIG. 9 or a network analyzer 81 of known construction. The network analyzer looks at the impedence of the circuit between the well 79 and the cantilever 78.

If the apparatus of FIG. 10 is exposed to the fluid that affects the sensitive member 73, the sensitive member undergoes a change in its physical properties and the resonance frequency of the cantilever 74 is thereby changed. This change in resonance frequency is sensed by the network analyzer. In addition, the amount of change can be determined by adjusting the variable frequency oscillator 80 until the new point of mechanical resonance is found.

Figure 11:
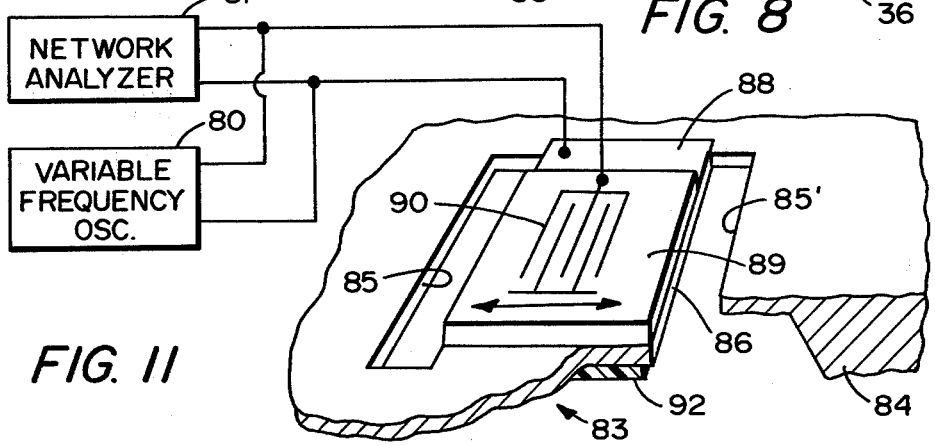
FIG. 11 is a perspective view, in cross-section and broken away, of a tenth embodiment of the present invention.

FIG. 11 illustrates a resonator structure 83 that utilizes surface acoustic waves for detecting the presence of a specific fluid. The apparatus includes a semiconductor substrate 84 such as either silicon dioxide or silicon. The bottom surface of the substrate is etched away in the manner described above so that a thin membrane is formed. Thereafter, the membrane is further etched to form two parallel slots 85 which define a doubly supported beam 86. The slots each present a sufficient air gap so that 100% of the surface acoustic waves are reflected. The top surface of the beam 86 is surmounted by a composite assembly that includes a thin gold layer 88 that forms an electrode, a piezoelectric layer 89 such as zinc oxide and a single interdigitated transducer 90. The entire composite assembly is thin compared with the wavelength of the surface acoustic waves that are propagated at the operating frequency of the transducer. The bottom surface of the beam 86 is covered by a sensitive member 92 which is carefully chosen to have a physical property that changes the resonance of the structure in the presence of the fluid to be detected. The apparatus acts as a surface acoustic wave resonator and is driven by a variable frequency oscillator 80 at the mechanical or acoustic resonance of the structure. Resonance is determined by a network analyzer 81 in the manner described above.

In operation, the interdigitated transducer 90, FIG. 11 launches plane waves in the lowest mode of vibration. The waves propagate toward the slots 85, 85' in both directions and when they hit lateral sides of the beam 86, they are reflected back by the air gaps. Only a plate mode is generated within the beam 86 and the only mode of wave propagation is the mode that is both launched and reflected. The waves in the beam interact with the sensitive member 92 in the same manner as described above in connection with FIG. 5. Resonance occurs when the interdigitated transducer is driven by the oscillator 80 with a signal having a period equal to an integral multiple of the wavelength of the mode of propagation set up in the membrane. Acoustic resonance is determined by the network analyzer 81.

If the sensitive member 92, FIG. 11 comes into contact with the specific fluid being sensed, the elastic properties of the member change. As a result the acoustic velocity of the waves set up in the beam 86 change and the resonance frequency of the apparatus likewise changes. The presence of the fluid being sensed is determined by the network analyzer 81 which indicates that the previously stable resonance frequency of the apparatus 83 has changed. The amount of change is determined by varying the driving frequency of the oscillator 80 and by determining the new resonance frequency.

It should be appreciated that although specific embodiments have been disclosed herein, the essential features of each embodiment can be interchanged. For example, the propagating medium 14, 36, 54 can be either gallium arsenide FIG. 6, or silicon with a piezoelectric layer 18, 40. Temperature compensation using dual paths, FIGS. 2 and 4 can be incorporated into the embodiments of FIGS. 5–8. Further, either oscillator circuits and frequency analyzers or time-delay measuring devices 28 can be used to determine the presence of the fluid being measured.

In addition, although the sensitive material 24,52 used herein is typically a polymer and is used for detecting gases, it is also contemplated that crystallites of certain materials that have an affinity for various vapors can be used. These materials are capable of absorbing many times their own weight. Examples of the materials are $CaCl_2$ which takes up moisture and activated charcoal (high-surface-area carbon) which absorbs CO and other lethal gases. Further, the apparatus of FIG. 11 can be used without the sensitive member and operated as a surface acoustic wave resonator. It can further be operated as a surface wave oscillator when coupled electrically to a suitable active electronic amplifier.

Other aspects, objects, and advantages of this invention can be obtained from a study of the drawings, the disclosure, and the appended claims.

We claim:

1. Apparatus for sensing the presence of a specific fluid, comprising:
   (a) a substrate in which surface acoustic waves can be propagated, said substrate having a planar top surface and a planar bottom surface opposite thereto;
   (b) a transmitting transducer located on said top surface for propagating surface acoustic waves in said substrate along a path;
   (c) a receiving transducer located on said top surface for receiving said surface acoustic waves propagated in said substrate along said path; and
   (d) a sensing member located on the bottom surface of the substrate in the path of the surface acoustic waves for interacting therewith and having a physical characteristic that varies the surface acoustic waves when in the presence of a specific fluid, said member interacts with the waves so that the presence of the fluid is sensed by the receiving transducer as a variation of the surface acoustic waves.

2. An apparatus as in claim 1 wherein the sensitive member varies the velocity of the surface acoustic waves and including means, connected to the receiving transducer, for measuring the variation in velocity of the waves along the path.

3. An apparatus as in claim 1 including a signal amplifier connected between the transmitting transducer and the receiving transducer, the amplifier forming a surface acoustic wave oscillator circuit with said path and substrate.

4. An apparatus as in claim 1 including a shield mounted on the top surface of the substrate for protecting said transmitting and receiving transducers from damage while said sensing member on the bottom surface of the substrate remains exposed.

5. An apparatus as in claim 1 wherein the planar top and bottom surfaces of the substrate have a separation approximately equal to the wavelength of the surface acoustic waves propagated in the substrate.

6. An apparatus as in claim 1 wherein the substrate is silicon and the surface acoustic waves are propagated in a piezoelectric film deposited thereon.

7. An apparatus as in claim 1 wherein said substrate is silicon, wherein the transducers are connected to the substrate by a piezoelectric film, and wherein the sensing member is located on the substrate out of contact with the piezoelectric film so that the surface acoustic waves are not propagated in the piezoelectric film while interacting with the sensitive member.

8. An apparatus as in claim 1 wherein the substrate is a piezoelectric material and the surface acoustic waves propagate therein.

9. A surface acoustic wave resonator, comprising:
   (a) a doubly supported beam in which surface acoustic waves can be propagated, said beam having two lateral sides each with a sufficient air gap to reflect said waves;
   (b) a transducer attached thereto for propagating surface waves laterally across the beam and for reflecting said waves off of said sides; and
   (c) means, connected to the transducer, for driving the transducer with a signal having a period equal to an integral multiple of the wavelength of a mode of wave propagation in the beam.

10. An apparatus as in claim 9 wherein said transducer is a single interdigitated transducer located laterally on the beam.

11. An apparatus as in claim 10 wherein said beam is thin compared with the wavelength of the surface wave propagated across the beam.

12. An apparatus as in claim 9 including means, connected to the transducer, for sensing mechanical resonance of the waves propagated in the beam.

13. An apparatus as in claim 9 wherein said beam is thin compared with the wavelength of the surface wave propagated across the beam.

14. Apparatus for sensing the presence of a specific fluid, comprising:
   (a) a substrate having a thinned membrane portion, said membrane portion having a planar top surface and a planar bottom surface opposite thereto;
   (b) means attached to the top surface of said membrane for vibrating said membrane at mechanical resonance and with a generally drum-head like vibration;
   (c) a sensing member located on the bottom surface of said membrane and having a physical characteristic that varies the mechanical resonance of the membrane when in the presence of a specific fluid; and
   (d) means for sensing mechanical resonance of the membrane when vibrated.

* * * * *